(12) United States Patent
Hoarau

(10) Patent No.: US 8,465,776 B2
(45) Date of Patent: Jun. 18, 2013

(54) GRANULE AND ORALLY DISINTEGRATING TABLET COMPRISING OXYCODONE

(75) Inventor: Didier Hoarau, Montreal (CA)

(73) Assignee: Ethypharm, Saint-Cloud Cedex (FR)

( * ) Notice: Subject to any disclaimer, the term of this patent is extended or adjusted under 35 U.S.C. 154(b) by 249 days.

(21) Appl. No.: 12/376,060

(22) PCT Filed: Jul. 31, 2007

(86) PCT No.: PCT/EP2007/057912
§ 371 (c)(1),
(2), (4) Date: Feb. 2, 2009

(87) PCT Pub. No.: WO2008/015220
PCT Pub. Date: Feb. 7, 2008

(65) Prior Publication Data
US 2009/0304792 A1    Dec. 10, 2009

Related U.S. Application Data

(60) Provisional application No. 60/821,449, filed on Aug. 4, 2006.

(51) Int. Cl.
*A61K 9/16* (2006.01)
*A61K 9/20* (2006.01)
*A61K 9/24* (2006.01)
*A61K 9/32* (2006.01)

(52) U.S. Cl.
USPC ........... 424/490; 424/497; 424/496; 424/464; 424/470; 424/472; 514/951

(58) Field of Classification Search
USPC ... 424/490, 497, 496, 464, 470, 472; 514/951
See application file for complete search history.

(56) References Cited

U.S. PATENT DOCUMENTS

| | | | |
|---|---|---|---|
| 5,464,632 A | 11/1995 | Cousin et al. | |
| 6,106,861 A | 8/2000 | Chauveau et al. | |
| 6,740,341 B1 * | 5/2004 | Holt et al. | 424/490 |
| 7,384,653 B2 * | 6/2008 | Wright et al. | 424/489 |
| 2003/0180361 A1 | 9/2003 | Oshlack et al. | |
| 2006/0134422 A1 | 6/2006 | Chenevier et al. | |
| 2006/0275364 A1 * | 12/2006 | Ahmed et al. | 424/464 |
| 2009/0022809 A1 * | 1/2009 | Kolhe et al. | 424/494 |
| 2009/0311320 A1 * | 12/2009 | Oury et al. | 424/465 |

FOREIGN PATENT DOCUMENTS

| | | |
|---|---|---|
| CN | 1747723 B | 5/2010 |
| EP | 0548356 B1 | 6/1993 |
| EP | 0553392 A1 | 8/1993 |
| EP | 0636364 A1 | 2/1995 |
| EP | 1003484 B1 | 11/2001 |
| EP | 1058538 B1 | 6/2002 |
| WO | 9846215 A1 | 10/1998 |
| WO | 9944580 A1 | 9/1999 |
| WO | 0006126 A1 | 2/2000 |
| WO | 0027357 A1 | 5/2000 |
| WO | 0051568 A1 | 9/2000 |
| WO | 03007802 A2 | 1/2003 |
| WO | 03077867 A2 | 9/2003 |
| WO | 2004069135 A2 | 8/2004 |

OTHER PUBLICATIONS

Hermos et al., "Characterizations of Long-term Oxycodone/Acetaminophen Prescriptions in Veteran Patients", Arch. Intern. Med., vol. 164, pp. 2361-2366, (2004).

Palangio et al., "Combination Hydrocodone and Ibuprofen Versus Combination Oxycodone and Acetaminophen in the Treatment of Moderate or Severe Acute Low Back Pain", Clinical Therapeutics, vol. 24, pp. 87-99 (2002).

Seager et al., "Drug-delivery products and the Zydis fast-dissolving dosage forms", J. Pharm. Pharmacol. (Abstract Only), (1998).

International Search Report for PCT/EP2007/057912.

* cited by examiner

*Primary Examiner* — Mina Haghighatian
(74) *Attorney, Agent, or Firm* — Caesar, Rivise, Bernstein, Cohen & Pokotilow, Ltd.

(57) ABSTRACT

The present invention relates to granules comprising oxycodone, as well as to orally disintegrating tablets including same and optionally acetaminophen.

24 Claims, No Drawings

GRANULE AND ORALLY DISINTEGRATING TABLET COMPRISING OXYCODONE

FIELD OF THE INVENTION

The present invention relates to taste-masked granules containing oxycodone, as well as orally disintegrating tablets comprising said granules and optionally acetaminophen.

BACKGROUND OF THE RELATED ART

Various orally disintegrating tablets are currently available on the market. These tablets include a disintegrant and usually a pharmaceutically active ingredient ("active ingredient") and disintegrate or dissolve without a chewing action in less than three minutes, usually in less than 60 seconds, upon contact with saliva, forming a suspension of small particles which is easy to swallow.

Once easily swallowed, the particles containing the active ingredient release the same most preferably into the stomach or into the upper part of the gastrointestinal tract.

This type of tablet is described, for example, in documents EP 548 356, EP 636 364, EP 1 003 484, EP 1 058 538, WO 98/46215, WO 00/06126, WO 00/27357 and WO 00/51568.

Orally disintegrating tablets are a convenient route for swallowing active agents since they do not require, but not exclude, absorbing water at the same time.

Owing to its ease of use, the orally disintegrating tablet is entirely suitable for ambulatory treatment, more particularly for certain patients and especially the elderly or young children, who have difficulties in swallowing such that they find it unpleasant, or even impossible, to ingest tablets or gel capsules, even with a simultaneous intake of liquid.

It is estimated that 50% of the population experiences such difficulties, with the possible consequence of the prescribed medicinal product not being taken and thus a major impact on the efficacy of the treatment (H. Seager, 1998, J. Pharm. Pharmacol. 50, 375-382).

In the case where the active ingredient has for instance a bitter or an unpleasant taste, the small particles may consist of coated granules containing the said active ingredient, thus preventing a bad taste from developing in the mouth. Such coating can also be provided to prevent the active ingredient from being prematurely released in the mouth or to ensure delayed release in the stomach. A typical coating for taste-masking is an aminoalkyl methacrylate copolymer sold by Röhm Pharma Polymers (Degussa) as EUDRAGIT® E 100 or EPO, namely dimethyl aminoethyl methacylate copolymer, comprising a functional group with tertiary amine.

This coating is insoluble at a pH above 5.5, thus remains intact in contact with saliva but is readily soluble in gastric juice, due to the protonation of the amine functions, thus releasing the active ingredient in an immediate manner in the stomach.

However, the Applicant has discovered that this copolymer is not suitable for making conventional coated granules for direct tableting from oxycodone in the form of a base or a pharmaceutically acceptable salt such as oxycodone hydrochloride which is prescribed to relieve pain.

It has been observed by the Applicant that the oxycodone content of such granules tends to decrease with time due to the degradation of oxycodone into oxidation by-products such as oxycodone N-oxide and oxymorphone. Without intending to be bound by any theory, it is believed that the nitrogen atom of the tertiary amines of the dimethylaminoethyl methacrylate units of Eudragit® E100 may form hydrogen bonding with the hydrogen atom of the ammonium function of oxycodone hydrochloride, which in turn could facilitate oxidation reactions. Peroxides or other contaminants, originating from other excipients or active ingredients, are also susceptible to induce oxidative degradation of oxycodone.

Now, it is preferable that the final tablets retain as much oxycodone for as long as possible under storage conditions. This is both so that the efficacy of the tablet remains high, and so that the degradents and impurities produced by the breakdown of the active ingredients remain low. Specifically, it is preferable that at least about 90% of the oxycodone, and more preferably at least about 95% of the oxycodone remain after storage for 14 days, and more preferably after 21 days at 80° C. dry heat.

Oxycodone is for instance marketed as conventional tablets alone as an hydrochloride salt under the trademark Roxicodone®, or in combination with acetaminophen, by ENDO PHARMACEUTICALS under the trademark Percocet®.

However, formulating orally disintegrating tablets including both oxycodone and acetaminophen proved to be difficult, since it has been discovered that acetaminophen can promote the degradation of an opiate such as oxycodone by direct interaction especially in moist conditions or in the presence of residual humidity.

It has also been observed that acetaminophen release was also slowed down when acetaminophen crystals were combined with oxycodone hydrochloride in taste masked granules prepared according to US 2006/0134422, further dispersed within an orally disintegrating tablet. Thus standard methods of isolating oxycodone from acetaminophen can delay the release of the two active agents and undesirably delay the onset of pain relief to the patient.

For the purposes of the present invention the expression "orally disintegrating tablets" refers to a tablet which disintegrates or dissolves in the mouth in less than 60 seconds, preferably in less than 40 seconds upon contact with saliva, forming therefore small particles which are easy to swallow.

The disintegration time here corresponds to the time between the moment when the tablet is placed on the tongue and the moment when the suspension resulting from the disintegration or dissolution of the tablet is swallowed.

Thus, there remains a need for orally disintegrating tablets in which a peroxide-sensitive active agent such as oxycodone can be included without experiencing any substantial degradation, either alone or in combination with acetaminophen.

Moreover, there remains a need for a means for orally delivering a stable form of oxycodone to the gastrointestinal tract while avoiding premature release thereof in the mouth.

In addition, it would be desirable to provide for an orally disintegrating tablet comprising both oxycodone and acetaminophen while offering not only stable oxycodone, but also a good dissolution rate of acetaminophen, i.e. a release of 85% wt of acetaminophen from a tablet including 325 mg thereof, in less than 10 minutes at any pH ranging from pH 1.2 to pH 6.8 and at least 90% release of acetaminophen at 15 min. It would also be desirable to provide for an orally disintegrating tablet comprising both oxycodone and acetaminophen while having a $C_{max}$ of acetaminophen between 4.5 and 6.8 ng/mL for a tablet including 10 mg oxycodone and 325 mg acetaminophen and providing for a fast dissolution rate of acetaminophen at an acidic pH, such as in the stomach.

The object of this invention is thus to propose new dosage forms of oxycodone enabling to solve the above needs.

SUMMARY OF THE INVENTION

Surprisingly, it has been discovered that the degradation of oxycodone could be prevented when oxycodone was formulated as specific coated granules optionally included in an orally disintegrating tablet.

Moreover, it has been discovered that oxycodone could be combined in a single orally disintegrating tablet with acetaminophen without degrading, provided that acetaminophen and oxycodone are not present in the same granules.

A first object of this invention thus pertains to granules comprising a neutral core coated with oxycodone or one of its pharmaceutically acceptable salts and at least a binding agent, said oxycodone coating being further coated with a subcoat comprising a compound soluble in gastric fluids; wherein said subcoat is further coated with a taste-masking coating comprising a polymer or copolymer with dialkylaminoalkyl (meth)acrylate units.

A second object of this invention relates to a process for the manufacture of the above granules, wherein a suspension of oxycodone in a hydroalcoholic medium is sprayed onto neutral cores.

A third object of this invention pertains to orally disintegrating tablets comprising: (a) granules comprising a neutral core coated with oxycodone or one of its pharmaceutically acceptable salts and at least a binding agent, said oxycodone coating being further coated with a subcoat comprising a compound soluble in gastric fluid; wherein said subcoat is further coated with a taste-masking coating comprising a polymer or copolymer with dialkylaminoalkyl(meth)acrylate units, and (b) at least one disintegrant and at least one soluble diluent agent, wherein said disintegrant comprises crospovidone.

According to a fourth object, this invention also relates to orally disintegrating tablets comprising: (a) granules comprising a neutral core coated with oxycodone or one of its pharmaceutically acceptable salts and at least a binding agent, said oxycodone coating being further coated with a subcoat comprising a compound soluble in gastric fluid; wherein said subcoat is further coated with a taste-masking coating comprising a polymer or copolymer with dialkylaminoalkyl (meth)acrylate units, (b) acetaminophen which is not included within oxycodone granules and may optionally be coated, and (c) at least one disintegrant and at least one diluent agent, wherein said disintegrant comprises crospovidone.

A fifth object of this invention pertains to a process for manufacturing said tablets, as well as the tablets thus obtained.

This process comprises the steps of:
(a) spraying onto neutral cores a suspension in a solvent of oxycodone or one of its pharmaceutically acceptable salts and at least one binding agent, so as to obtain pellets,
(b) applying a subcoat onto said pellets, by spraying thereon a compound soluble in gastric fluid mixed with a solvent, thus obtaining coated pellets,
(c) optionally drying said coated pellets,
(d) applying onto said coated pellets a taste-masking coating comprising a polymer or copolymer with dialkylaminoalkyl(meth)acrylate units and optionally a pore-forming agent, so as to obtain granules,
(e) optionally applying an antistatic coating onto said granules,
(f) mixing acetaminophen, optionally applied onto neutral cores and/or coated, with said granules, at least one disintegrant comprising crospovidone and at least one soluble diluent agent, so as to obtain a powder mixture, and
(g) tableting said powder mixture,
wherein the solvent used in at least one of steps (a) and (b) is a hydroalcoholic solvent.

A sixth object of this invention is directed to an orally disintegrating tablet comprising acetaminophen and oxycodone as the only active ingredients, said tablet having an oxycodone content, after dry storage at 80° C. for 14 days, preferably for 21 days, of at least about 90%, preferably of at least about 95%, of the initial oxycodone content before storage.

A seventh object of this invention pertains to the use of the aforementioned granules or tablets for the management of breakthrough pain or more generally for the relief of moderate to severe pain and also for the manufacture of an analgesic medicament for oral administration in such use. It also pertains to a method for reducing pain comprising oral administration of granules or tablets as described above.

DETAILED DESCRIPTION OF PREFERRED EMBODIMENTS

Oxycodone can be used as such or as a pharmaceutically acceptable salt thereof. The term "pharmaceutically acceptable salts" is intended to mean the derivatives of oxycodone in which the base compound is converted to its salt with an organic or inorganic acid, examples of which comprise acetic, ascorbic, benzenesulfonic, benzoic, boric, camphorsulfonic, citric, ethanesulfonic, fumaric, gluconic, glutamic, glutaric, glycerophosphoric, hydrobromic, hydrochloric, hydroiodic, isethionic, lactic, maleic, malic, malonic, mandelic, methanesulfonic, mucic, nitric, oxalic, pamoic, pantothenic, phosphoric, salicylic, succinic, sulphuric, tartaric, terephthalic, p-toluenesulfonic acid, and the like.

Preferred oxycodone salts are oxycodone hydrochloride and oxycodone terephthalate.

In the following, "oxycodone" will be used indifferently for oxycodone or pharmaceutically acceptable salts thereof.

The amount of oxycodone or its salt may range from about 1% to 50%, preferably from about 5% to 25% by weight relative to the weight of the neutral core. According to a preferred embodiment, it is possible to prepare oxycodone loaded granules of different strengths in order to accommodate the different dosage strengths of the final tablets. Actually, in a preferred embodiment low strength granules containing about 5% to about 6% by weight of oxycodone (relative to the total weight of the drug loaded granules) may be used to prepare 2.5 mg and 5 mg dosage units and high strength granules containing about 10% to about 12% of oxycodone (relative to the total weight of the drug loaded granules) may be used to prepare 7.5 mg and 10 mg dosage units. In this way, the tablet strength may be varied without making the tablet unpalatably large.

The granules according to this invention comprise a first layer comprising oxycodone which is applied onto neutral cores.

The neutral core may comprise any chemically and pharmaceutically inert excipient, existing in particle form, either crystalline or amorphous, for example sugars or sugar derivatives such as lactose, sucrose, hydrolyzed starch (maltodextrins), celluloses such as microcrystalline cellulose, or mixtures thereof such as sucrose and starch; or mixtures thereof with a cellulose base.

The oxycodone coating may be applied by spraying a suspension or solution of oxycodone onto neutral cores, preferably in a fluidized-air coating device. Preferably, oxycodone will be used as a suspension in a hydroalcoholic medium. It has indeed been observed that using a hydroalcoholic medium instead of an aqueous medium provided for greater stability of the oxycodone. The hydroalcoholic medium advantageously comprises water and ethanol, for instance in a ratio of ethanol to water ranging from about 60:40 to about 92:8 and more preferably of about 75:25 to about 85:15.

The present inventors have discovered that this solvent reduced oxycodone degradation, as evidenced by the following Examples.

The oxycodone layer also comprises a binding agent or binder. Said binder is conventionally used in proportions that can range up to 95% by weight relative to the dry weight of the coating, preferably up to 50% by weight relative to the dry weight of the oxycodone coating.

Its function is to bind the active ingredient and other optional pharmaceutical excipients to the neutral core without loss of material, thus forming a homogeneous layer of pharmaceutically active ingredient, evenly distributed around the neutral core.

The binder can be chosen from the group consisting of cellulose-based polymers, such as hydroxypropylmethylcellulose, hydroxypropylcellulose and hydroxyethylcellulose; acrylic polymers; polyvinyl alcohols; alginic acid or sodium alginate; starch or pregelatinized starch; sucrose and derivatives thereof; guar gum; polyethylene glycols, and mixtures and copolymers thereof, for instance a graft copolymer of polyvinyl alcohol and polyethylene glycol, such as sold by BASF under trade name KOLLICOAT® IR.

Hydroxypropylmethylcellulose (also referred to as "HPMC" hereunder) is the preferred binder according to this invention. It can preferably be chosen from those for which the apparent viscosity (aqueous solution at 2% m/m, at 20° C., USP method) is between 2.4 and 18 mPa·s, and even more preferably between 2.4 and 5 mPa·s.

The binder, when dissolved in a hydroalcoholic solvent, is advantageously present in a proportion that can range up to 90%, preferably of between 5% and 60% and more preferably of about 50% by weight relative to the weight of oxycodone.

Moreover, the first (oxycodone) layer may also comprise one or more pharmaceutically acceptable excipients, apart from the binding agent.

The pharmaceutically acceptable excipients optionally present may be chosen from surfactants, antistatic agents, lubricants, and mixtures thereof.

The surfactant, which is optionally present in the oxycodone coating, can be chosen from cationic, anionic, nonionic or amphoteric agents, alone or as a mixture.

The surfactant can be chosen, for example, from compounds such as sodium lauryl sulphate, the monooleate, the monolaurate, the monopalmitate, the monostearate, the trioleate, the tristearate or any other ester of polyoxyethylenated sorbitan, preferably Tween® 20, 40, 60 or 80, glycerides of polyoxyethylenated fatty acids, these fatty acids being saturated or unsaturated and composed of at least 8 carbon atoms, poloxamers, such as poloxamer 188, ethylene oxide/propylene oxide block copolymers, such as Pluronic® F68 or F87, lecithin, stearyl alcohol, cetearyl alcohol, cholesterol, polyoxyethylenated castor oil, fatty alcohol polyoxyethylenated ethers, such as the Brij® products, and polyoxyethylenated stearates.

The surfactant is advantageously present in a proportion that can range up to 20%, preferably of between 0.1 and 20% by weight relative to the total dry weight of the coating.

The antistatic agent can be used in a proportion that can range up to 10% by weight, relative to the dry weight of the coating applied around the neutral core. The antistatic agent may be chosen from the group consisting of: colloidal silica and preferably precipitated silica, micronized or non-micronized talc, and mixtures thereof.

The lubricant may be selected from the group comprising magnesium, zinc, and calcium stearate, stearic acid, talc, pyrogenic silica, hydrogenated vegetable oils, sodium stearylfumarate, micronized polyoxyethylene glycol (micronized Macrogol 6000), leucine, sodium benzoate, and mixtures thereof.

As mentioned above, in the granules according to this invention, the first layer comprising oxycodone is further coated by a separating layer (also referred to as "subcoat") between the coating layer comprising oxycodone and the taste-masking polymeric layer, wherein said subcoat comprises at least a compound soluble in gastric fluid, i.e. in highly acidic conditions (pH comprised between 1 and 2), preferably a polymer which can be chosen among the binding polymers or copolymers mentioned above. An example of a copolymer that can be used in the subcoat is a graft copolymer of polyvinyl alcohol and polyethylene glycol, such as sold by BASF under the trade name KOLLICOAT® IR. A preferred polymer is hydroxypropylmethylcellulose. The polymer or copolymer, included within the subcoat, acts as a separating layer in order to avoid direct contact between the oxycodone layer and the taste-masking polymer, and dissolves rapidly without altering oxycodone release. The subcoat layer may also comprise an antistatic agent such as those listed previously.

The subcoat is advantageously present in a proportion that can range up to 50%, preferably of between 5% and 30% by weight relative to the weight of oxycodone coated cores.

The subcoat can be applied by conventional means, such as in a fluidized-air coating device, by spraying a solution or a dispersion of binder in an aqueous or preferably in a hydroalcoholic medium onto the cores coated with oxycodone. The hydroalcoholic medium advantageously comprises water and ethanol, for instance in a ratio of ethanol to water ranging from about 60:40 to about 92:8 and more preferably of about 85:15.

This subcoat is itself coated by a taste-masking coating layer comprising a polymer or copolymer comprising dialkylaminoalkyl(meth)acrylate units, such as dimethylaminoethyl methacrylate units. This polymer can be, for instance, a copolymer of dimethylaminoethyl methacrylate, methylmethacrylate and n-butyl methacrylate, such as the copolymer sold by RÖHM PHARMA under the trade names EUDRAGIT® E100 and EPO.

The taste-masking coating preferably further includes a pore-forming agent which can be a hydrophilic polymer soluble in gastric fluids, such as hydroxypropylmethylcellulose or other polymers used as binders such as polyvinylpyrrolidone, polyvinylalcohol, polyethyleneglycols, or a soluble agent, preferably chosen from the group of sugars such as sucrose, lactose or dextrose, of polyols such as mannitol, sorbitol or lactitol, or of organic acids and their salts such as citric acid, tartaric acid, succinic acid, or else of inorganic salts such as sodium chloride. A preferred pore-forming agent is hydroxypropylmethylcellulose.

The pore-forming agent, which is optionally present in the taste-masking coating, can be used in a proportion that can range up to 50%, preferably of between 5% and 30% by weight relative to the total dry weight of the taste-masking coating ingredients.

It has indeed been shown that the provision of this pore-forming agent within the taste-masking coating improved the release rate of oxycodone from the granule at a pH equal or greater than pH 5.5 such as in the intestine, by increasing the permeability of the taste-masking film coating and thus preventing the slowing down of oxycodone release when the granules directly pass into the intestine, which may undesirably occur when the patient ingesting the granule has a fast digestion and/or is stressed.

The amount of pore-forming agent in the taste-masking coating and the total amount of taste-masking coating relative to the total weight of the oxycodone granule with its subcoat have to be chosen so as to provide taste-masking effectiveness during the short period of time in the saliva and to ensure, following the swallowing of the granules, fast dissolving in pH ranging from pH 1.2 to pH 6.8. The ratio of the taste-masking coating to the total dry weight of ingredients comprising the oxycodone granule with its subcoat ranges from about 10:90 to about 50:50 and more preferably of about 20:80 (or 25%).

The taste-masking layer may also comprise an antistatic agent, such as those listed above.

The granules according to this invention can advantageously be used in the manufacture of orally disintegrating tablets.

To this end, the granules described above can be mixed with at least one disintegrant and at least one soluble diluent agent preferably having binding properties and then directly compressed so as to form tablets.

The compression force is adjusted so as to obtain a friability, measured according to the method of the European Pharmacopoeia, of less than 2% w/w and preferably less than 1.5% w/w, and so as to allow a disintegration time of the tablet in the mouth under the action of saliva of less than or equal to 60 seconds and preferably less than or equal to 40 seconds.

Hardness is preferably comprised between 10 and 180 N, preferably between 15 and 100 N and more preferably between 50 and 80 N, measured according to the method of the European Pharmacopoeia (2.9.8).

The present invention thus also pertains to orally disintegrating tablets comprising: (a) granules comprising a neutral core coated with oxycodone or one of its pharmaceutically acceptable salts and at least a binding agent, said oxycodone coating being further coated with a subcoat comprising a compound soluble in gastric fluid; wherein said subcoat is further coated with a taste-masking coating comprising a polymer or copolymer with dialkylaminoalkyl(meth)acrylate units, and (b) at least one disintegrant and at least one soluble diluent preferably having binding properties, wherein said disintegrant comprises crospovidone.

The above tablets can include, for instance, from 1 to 20 mg oxycodone hydrochloride, preferably from 2.5 to 10 mg oxycodone hydrochloride, per tablet.

The disintegrating agent may further comprise crosslinked sodium carboxymethylcellulose, which is referred to as croscarmellose. The preferred disintegrant is crospovidone alone.

Usually, the disintegrant represents from 1 to 15%, and preferably from 2 to 10% and the soluble diluent agent represents from 20 to 80%, and preferably from 25 to 40% of the total weight of the tablet.

The soluble diluent agent may be a polyol having less than 13 carbon atoms and being present either in the form of a directly compressible product with an average particle size from 100 to 500 μm, or in the form of a powder with an average particle size of less than 100 μm, or mixtures thereof.

In a preferred embodiment, said polyol is selected from the group consisting of mannitol, xylitol, sorbitol, and maltitol. In the case where there is only one soluble diluent agent, it is used in the form of a directly compressible product, whereas, in the case where there are at least two soluble diluent agents, one is present in a directly compressible form and the other in a powder form, it then being possible for the polyol to be the same, the ratio of directly compressible polyol and of powdered polyol being 99:1 to 20:80, preferably 80:20 to 20:80.

Preferably, the soluble diluent agent with binding properties is a mixture of mannitol in the form of a powder with an average particle size of less than 100 μm, preferably Mannitol 60 and directly compressible mannitol with an average particle size from 100 to 500 μm, such as Mannitol 300.

It has been observed that crospovidone had a stabilizing effect on the degradation of oxycodone when the orally disintegrating tablets are stored under dry atmosphere. The tablets according to this embodiment of the invention are thus preferably packaged in sealed containers such as blisters. In addition, they can advantageously include an anti-oxidant agent so as to better protect oxycodone from degradation which could occur under moist conditions as a result of crospovidone degradation.

Examples of suitable anti-oxidants include ascorbic acid and its salts and esters, such as sodium ascorbate and ascorbyl palmitate; tocopherol and its esters such as tocopherol acetate; and mixtures thereof.

Usually, the anti-oxidant is present from 0.2 to 1 wt % relative to the total weight of the tablet. It can also be expressed as a ratio to the crospovidone used. In this regard, it is preferred that the anti-oxidant represents from 1 to 5% of the weight of the crospovidone used.

In particular, it has been found that ascorbyl palmitate efficiently prevented degradation of crospovidone under moist conditions and thus protected oxycodone from oxidation. The amount of ascorbyl palmitate that can be included in the tablets according to this invention can range from 0.2 to 1% w/w relative to the total weight of the tablet. It can also be expressed as a ratio to the crospovidone used. In this regard, it is preferred that ascorbyl palmitate represents from 1 to 5% of the weight of the crospovidone used.

The orally disintegrating tablet can also include various additives such as a lubricant, a swelling agent, a permeabilizing agent, a sweetener, a flavouring agent, a colorant and their mixtures.

The lubricant may be selected from those listed previously.

The amount of lubricant may range from 0.2 to 2% (weight of lubricant/total weight of the tablet), preferably from 0.5 to 1.5%. The lubricant can be dispersed within the powder bed compressed into a tablet or, according to an advantageous embodiment, the totality of the lubricant can be dispersed on the surface of the tablet.

The swelling agent may be selected from the group comprising native and modified starches.

The permeabilizing agent may be selected from the group comprising precipitated silica, maltodextrins, beta-cyclodextrin, and mixtures thereof. The permeabilizing agent allows the creation of a hydrophilic network which facilitates the penetration of saliva and hence contributes to better disintegration of the tablet. The proportion of permeabilizing agent relative to the weight of the tablet is preferably from 0.5% to 5% by weight.

The sweetener may be selected from the group comprising in particular aspartame, acesulfam potassium, sodium saccharinate, neohesperidine dihydrochalcone, sucralose, monoammonium glycyrrhizinate, and mixtures thereof.

The flavouring agents and colorants are those conventionally used in pharmacy for the preparation of tablets.

These excipients will usually amount to less than 10 weight percent relative to the total weight of the tablet, preferably from 0.1 to 5%, even more preferably from 0.2 to 4.5%.

Moreover, it has been found that acetaminophen could be included within said tablets, provided that it is separated from the above-described granules coated with oxycodone. In this way, both active ingredients can be included in the same tablet while avoiding incompatibility problems between them.

This invention thus also relates to orally disintegrating tablets comprising: (a) granules comprising a neutral core coated with oxycodone or one of its pharmaceutically acceptable salts and at least a binder, said oxycodone coating being further coated with a subcoat comprising a compound soluble in gastric fluid; wherein said subcoat is further coated with a taste-masking coating comprising a polymer or copolymer with dialkylaminoalkyl(meth)acrylate units, (b) acetaminophen which is not included within said granules, and (c) at least one disintegrant and at least one diluent, wherein said disintegrant comprises crospovidone.

In a preferred embodiment, the oxycodone and acetaminophen tablet further comprises an anti-oxidant. Suitable anti-oxidants are those described above, whereby ascorbyl palmitate is preferred. The amounts of anti-oxidant and in particular ascorbyl palmitate are those described above.

Acetaminophen can be provided as crystals or as granules wherein acetaminophen can be coated with a taste-masking coating. The excipients included within this taste-masking coating can be the same as listed above. In this case, the taste-masking coating of the oxycodone granules and the taste-masking coating of the acetaminophen granules can be the same or different.

In a preferred embodiment, the crystals of acetaminophen are granulated with a binder and the obtained granules are coated with taste-masking coating.

In a most preferred embodiment, the crystals of acetaminophen are directly coated with a taste-masking coating.

The tablet can include, for instance, from 1 to 20 mg oxycodone, preferably from 2.5 to 10 mg oxycodone, per tablet.

The above-mentioned tablets can contain from 80 to 750 mg acetaminophen, per tablet.

The tablet may further include the same additives as those described in relation with the acetaminophen-free tablet described above The tablets according to the invention disintegrate in the mouth upon contact with saliva in less than 60 seconds, preferably in less than 40 seconds, forming a suspension which is easy to swallow.

These tablets, as well as the granules described previously, can be used in the relief of moderate to severe pain, such as in the management of breakthrough pain, in particular breakthrough cancer pain, by oral administration. Breakthrough pain means a transitory flare of pain of moderate to severe intensity occurring on a background of otherwise controlled pain.

Granules may for instance be administered as such, packaged in pouches, or in the form of capsules.

The invention will be understood more clearly from the following Examples which are not intended to restrict in any way the scope of this invention.

EXAMPLES

Example 1

Preparation of Granules Entrapping Oxycodone

Neutral cores were introduced into a fluid bed processor and a suspension of oxycodone hydrochloride, hydroxypropylmethyl cellulose (HPMC) as a binder in a solvent of water and ethanol was sprayed on the neutral cores. The composition of oxycodone pellets is given in Table 1 for Low and Hi strengths. The oxycodone amount entrapped in the Hi and Low strength pellets is of about 11.55% and 5.78% by weight respectively. A subcoat was then applied to the oxycodone pellets. The subcoat contained HPMC and silicon dioxide (as an antistatic) in a water/ethanol solvent as shown in Table 2 (the composition is the same whatever the strength). After drying, the granules were again introduced to the fluid bed processor and coated with a taste-masking coating of Eudragit® E100 acrylic polymer, HPMC and silicon dioxide in a water/ethanol solvent as shown in Table 3 (the composition is the same whatever the strength). In a last step, before discharging the taste-masked oxycodone granules, an antistatic solution composed of a suspension of silicon dioxide in ethanol is sprayed into the fluid bed processor. The composition is given in table 4. The oxycodone amount entrapped in the final granules is of about 3.8% and 7.7% by weight for the Low and Hi strength granules respectively.

TABLE 1

Composition of oxycodone hydrochloride pellets

| MATERIALS | 2.5/5 MG STRENGTHS (LS) | | 7.5/10 MG STRENGTHS (HS) | |
| --- | --- | --- | --- | --- |
| | % | TOTAL WEIGHT (KG) | % | TOTAL WEIGHT (KG) |
| Neutral cores | 91.33 | 15.20 | 82.67 | 13.76 |
| LAYERING SOLUTION | | | | |
| Oxycodone | 5.78 | 0.96 | 11.55 | 1.92 |
| HPMC | 2.89 | 0.48 | 5.78 | 0.96 |
| Water | n/a* | 2.93* | n/a* | 5.86* |
| Ethanol | n/a* | 10.63* | n/a* | 21.26* |
| Total (dry) | 100.00 | 16.64 | 100.00 | 16.64 |

*solvent removed during process

TABLE 2

Composition of oxycodone pellets coated with a subcoat

| | 2.5-10 MG STRENGTHS | |
| --- | --- | --- |
| MATERIALS | % | TOTAL WEIGHT (KG) |
| Oxycodone pellets | 83.5 | 16.64 |
| SUBCOATING SOLUTION | | |
| HPMC | 15.0 | 3.00 |
| Syloid F244P | 1.5 | 0.30 |
| Water | n/a* | 4.05* |
| Ethanol | n/a* | 22.95* |
| Total (dry) | 100.00 | 19.94 |

*solvent removed during process

TABLE 3

Excipients used in the taske-masking coating

| | 2.5-10 MG STRENGTHS | |
|---|---|---|
| MATERIALS | % | TOTAL WEIGHT (KG) |
| Oxycodone granules | 79.74 | 19.94 |
| COATING SOLUTION | | |
| Eudragit E100 | 14.74 | 3.69 |
| HPMC | 3.68 | 0.92 |
| Syloid F244P | 1.84 | 0.41 |
| Water | n/a* | 14.19* |
| Ethanol | n/a* | 21.28* |
| Total | 100.00 | 24.96 |

*solvent removed during process

TABLE 4

Excipients used in the antistatic suspension applied on the taste-masked oxycodone granules

| | 2.5-10 MG STRENGTHS | |
|---|---|---|
| MATERIALS | % | TOTAL WEIGHT (KG) |
| Taste-masked oxycodone granules | 99.80 | 24.96 |
| ANTISTATIC SOLUTION | | |
| Syloid F244P | 0.20 | 0.05 |
| Ethanol | n/a* | 0.83* |
| Total | 100.00 | 25.01 |

*solvent removed during process

Example 2

Preparation of Orally Disintegrating Tablets

Acetaminophen (APAP) crystals were introduced into a fluid bed processor and a suspension containing Eudragit® E100 acrylic polymer, Eudragit® NE30D acrylic polymer, and silicon dioxide in ethanol was sprayed on the APAP. The total amount of coating represents 6% in weight relative to the initial weight of APAP crystals.

The coated APAP crystals were mixed with the oxycodone-coated neutral cores from Example 1 and with excipients, as listed in the table below, and tableted in accordance with standard tableting procedures for making orally disintegrating tablets.

A Sviac 6 stations press was used with the following parameters (table 5). Table 6 presents the recommended specifications for tablet characteristics.

TABLE 5

Example of press setting for a Sviac PR-6

| PARAMETERS | VALUE |
|---|---|
| Turret speed | 25 rpm |
| Feed frame speed | 10 rpm |
| Punch diameter | 15 mm |

TABLE 6

Recommended specifications for tablet physical characteristics

| PARAMETERS | TARGET | RANGE |
|---|---|---|
| Tablet weight | 1050 mg | USP |
| Tablet hardness | 65N | 50-80N |
| Tablet thickness | 5.60 mm | 5.50-5.75 mm |
| Friability | NMT 1.5% | Release NMT 1.5% Stability NMT 2% |
| Disintegration time in mouth | NMT 30 s | NMT 45 s |
| Water content | NMT 2.0% | Release NMT 2.0% Stability NMT 3.0% |

The composition of the compressed tablets is shown in the following Table 7.

TABLE 7

Composition of orally disintegrating tablets containing taste-masked oxycodone granules and taste-masked APAP granules

| Materials | % |
|---|---|
| Coated oxycodone pellets | 9.51 |
| Coated APAP crystals (6% coating) | 32.85 |
| Mannitol 60 | 14.22 |
| Mannitol 300 | 14.22 |
| Microcrystalline cellulose PH102 | 10.00 |
| Crospovidone CL | 15.00 |
| Sucralose | 1.00 |
| Prosweet | 0.38 |
| Peppermint flavor | 0.75 |
| Silicon Dioxide 244 FP | 0.50 |
| Sodium Stearyl Fumarate | 1.50 |
| Red # 40 aluminium lake | 0.07 |
| Total | 100.00 |

Example 3 (Comparative)

Preparation of Granules Comprising Oxycodone and Acetaminophen

APAP crystals and silicon dioxide were introduced into a fluidized air bed installation and a layering solution of oxycodone dissolved in a solution of HPMC in water was sprayed thereon. The coated crystals were then reintroduced into a fluidized bed coater and overcoated using a coating suspension of Eudragit® E100 acrylic polymer in 95% ethanol with silica. The resulting coated granules were then dried. The composition of APAP granules coated with oxycodone and further coated with the taste-masking coating (for a final strength of 325 mg/2.5 mg) is given in Table 8.

TABLE 8

Composition of APAP/oxycodone taste-masked granules

| Materials | % |
|---|---|
| Acetaminophen | 82.33 |
| Silicon Dioxide 244 FP | 0.25 |
| OXYCODONE LAYERING SOLUTION | |
| HPMC | 0.28 |
| Oxycodone HCl | 0.63 |
| Purified water | n/a* |

TABLE 8-continued

Composition of APAP/oxycodone taste-masked granules

| Materials | % |
|---|---|
| COATING SOLUTION | |
| Eudragit E100 | 15.0 |
| Silicon Dioxide 244 FP | 1.51 |
| Ethanol | n/a* |

*solvent removed during process

Example 4 (Comparative)

Preparation of Orally Disintegrating Tablets

The granules obtained in Example 3 were blended with aspartame, peppermint, colorant, mannitol, crospovidone, microcrystalline cellulose and silica. The blend was then compressed into an orally disintegrating tablet according to conventional tabletting processes. The composition of the tablets is summarized in Table 9 below.

TABLE 9

| Table Composition | 2.5 mg Oxycodone HCl/325 mg APAP Weight (mg/tablet) | 10 mg Oxycodone HCl/325 mg APAP Weight (mg/tablet) |
|---|---|---|
| Granules | | |
| Acetaminophen | 325.0 | 325.0 |
| Oxycodone HCl | 2.5 | 10.0 |
| HPMC | 1.1 | 4.3 |
| Eudragit E100 | 59.2 | 60.9 |
| Silicon dioxide | 12.2 | 12.2 |
| Ethyl alcohol | QD | QD |
| Purified water | QD | QD |
| Tableting excipients | | |
| Mannitol | 399.8 | 387.5 |
| Crospovidone CL | 105.0 | 105.0 |
| Microcrystalline cellulose | 105.0 | 105.0 |
| Aspartame powder | 21.0 | 21.0 |
| Magnesium stearate | 13.1 | 13.1 |
| Peppermint | 5.3 | 5.3 |
| Colorant | 0.7 | 0.7 |
| Total Tablet Weight (mg) | 1050 | 1050 |

Example 5

Assessment of the Dissolution Rate of Acetaminophen and Oxycodone

The tablets produced according to Example 2 (invention) and 4 (comparative) were tested for their dissolution properties at a pH near the pH of the saliva. Dissolution using USP type 2 (paddle) dissolution apparatus at 100 rpm yielded the results shown in Tables 10 and 11 below, for acetaminophen and oxycodone respectively.

TABLE 10

| | Dissolution (%) of acetaminophen | |
|---|---|---|
| Time (mn) | Example 2 pH 6.8 | Example 4 pH 6.8 |
| 2.5 | 56 | 8.3 |
| 7.5 | 89 | 20.8 |
| 15 | 94 | 58.3 |
| 30 | 98 | 93.75 |

As may be seen from this Table, the dissolution of tablets made in accordance with this invention was much faster than with the comparative tablets.

Moreover, the $C_{max}$ of acetaminophen in the comparative tablets of Example 2 was 4.4 ng/mL for the tablets containing 2.5 mg oxycodone and 4.0 ng/mL for the tablets comprising 10 mg oxycodone. At pH 1-2 (close to that of gastric juices), it took 27 min to release 85% of APAP in the tablets containing 2.5 mg oxycodone and 12.9 min in the tablets containing 10 mg oxycodone. This slow dissolution rate of APAP is expected to result in too slow an absorption rate of this drug.

TABLE 11

| | Dissolution (%) of oxycodone | |
|---|---|---|
| Time (mn) | Example 2 pH 6.8 | Example 4 pH 6.8 |
| 0 | 0 | 0 |
| 5 | 97 | 33 |
| 10 | 100 | 74 |
| 15 | 100 | 81 |
| 30 | 100 | 90 |

This table shows that the addition of a pore-forming agent in the taste-masking coating of oxycodone granules results in a significant increase in the dissolution rate of oxycodone, especially at a pH greater than 5.5 such as pH 6.8. The addition of the pore-forming agent provides oxycodone taste-masked granules with pH-independent drug release profiles.

Example 6

Assessment of the Stability of Oxycodone—Comparison with Oxycodone Coated Acetaminophen Crystals Acetaminophen crystals were introduced into a fluid bed processor and a suspension of oxycodone, hydroxypropylmethyl cellulose (HPMC) as a binder and a solvent of water and ethanol was sprayed on the crystals. The granules were prepared by using a Mini-Glatt equipment with 100 g of support and a layering duration of 30 min at 25° C. The solvent contained 4 g water and 40.5 g ethanol. The composition and process parameters mentioned in Table 11 below were used.

The above procedure is repeated using neutral cores instead of acetaminophen crystals. The composition and process parameters mentioned in Table 12 below were used.

TABLE 12

| | Compositions tested | |
|---|---|---|
| Excipients | Composition A (% dry) | Composition B (% dry) |
| APAP crystals | 98.91% | 0 |
| Neutral cores | 0 | 98.91% |

TABLE 12-continued

Compositions tested

| Excipients | Composition A (% dry) | Composition B (% dry) |
|---|---|---|
| Oxycodone | 0.76% | 0.76% |
| HPMC 603 | 0.33% | 0.33% |

The granules thus obtained were stored in forced degradation conditions (80° C., dry heat) and the amount of oxycodone remaining as a function of time, relative to the initial content of oxycodone, was then assessed by HPLC.

The results showed no significant change in the oxycodone content of Composition B after 7 days, whereas it dropped to below 95% for Composition A. Moreover, the oxycodone content was also stable when granules of Composition B were prepared at 50° C. using an aqueous solvent, whereas it was only around 86% for granules of Composition A prepared under the same conditions.

This experiment demonstrates that oxycodone is more stable when coated on neutral cores than on acetaminophen crystals. This degradation of oxycodone is thought to be due to acetaminophen, which has been shown to degrade itself when in solution.

Example 7

Assessment of the Stability—Comparison with Granules without Subcoat

Oxycodone coated granules were prepared as described in Example 6 composition B, except that these granules were further coated with a taste-masking coating of Eudragit® E100 acrylic polymer and silicon dioxide (Syloid 244) in ethanol. These granules will be designated hereafter as Granules C. Their composition is given in Table 13 below.

TABLE 13

Composition of coated oxycodone granules without subcoat

| Excipients | Granules C Weight (g) | % |
|---|---|---|
| Oxycodone loaded granules (3.8% w/w oxycodone) | 120.00 | 79.74 |
| Eudragit E100 | 22.18 | 14.74 |
| HPMC | 5.54 | 3.68 |
| Syloid 244 | 2.77 | 1.84 |
| Purified water | 85.38 | n/a* |
| Ethanol | 128.06 | n/a* |
| TOTAL (Dry Mat.) | 150.49 | 100 |

*solvent removed during process

Similar granules were also prepared, which further contained a subcoat as described in Example 1 above, between the oxycodone coating and the taste-masking coating. These granules will be designated hereafter as Granules D. Their composition is given in table 14 below.

TABLE 14

Composition of oxycodone coated granules with protective subcoat

| Excipients | Granules D Weight (g) | % |
|---|---|---|
| Oxycodone loaded granules (3.8% w/w oxycodone) | 900.00 | 66.6 |
| Suspension for subcoat | | |
| HPMC | 161.68 | 12.0 |
| Syloid 244 | 16.17 | 1.2 |
| Purified water | 218.3 | n/a* |
| Ethanol | 1237.1 | n/a* |
| Suspension for coating | | |
| Eudragit E100 | 199.24 | 14.7 |
| HPMC | 49.74 | 3.7 |
| Syloid 244 | 24.87 | 1.8 |
| Purified water | 766.89 | n/a* |
| Ethanol | 1150.28 | n/a* |
| TOTAL (Dry Mat.) | 1351.7 | 100 |

*solvent removed during process

Granules C only contained around 80% oxycodone after 21 days at 80° C., whereas Granules D still contained 95% oxycodone at that time.

Moreover, tablets were prepared with Granules D as described in Example 2 (Table 15) and compared with similar tablets prepared with Granules C not containing a subcoat (Table 16).

TABLE 15

Composition of orally disintegrating tablets including oxycodone granules with a subcoat

| Materials | % |
|---|---|
| Coated oxycodone pellets (Granules D) | 7.20 |
| Coated APAP crystals (6% coating) | 26.53 |
| Mannitol 60 | 18.53 |
| Mannitol 300 | 18.54 |
| Microcrystalline cellulose PH102 | 10.00 |
| Crospovidone CL | 15.00 |
| Sucralose | 1.00 |
| Prosweet | 0.38 |
| Peppermint flavor | 0.75 |
| Silicon Dioxide 244 FP | 0.50 |
| Sodium Stearyl Fumarate | 1.50 |
| Red # 40 aluminium lake | 0.07 |
| Total | 100.00 |

TABLE 16

Composition of orally disintegrating tablets containing oxycodone granules without a subcoat

| Materials | % |
|---|---|
| Coated oxycodone pellets (Granules C) | 6.28 |
| Coated APAP crystals (6% coating) | 26.53 |
| Mannitol 60 | 18.99 |
| Mannitol 300 | 18.99 |
| Microcrystalline cellulose PH102 | 10.00 |
| Crospovidone CL | 15.00 |
| Sucralose | 1.00 |
| Prosweet | 0.38 |
| Peppermint flavor | 0.75 |
| Silicon Dioxide 244 FP | 0.50 |

TABLE 16-continued

Composition of orally disintegrating tablets containing oxycodone granules without a subcoat

| Materials | % |
|---|---|
| Sodium Stearyl Fumarate | 1.50 |
| Red # 40 aluminium lake | 0.07 |
| Total | 100.00 |

After 21 days at 80° C. dry heat in blister pockets, the tablets including a subcoat still contained about 95% oxycodone, whereas the comparative tablets without subcoat only contained about 70% oxycodone.

This experiment makes clear that acrylic polymers bearing amino side groups, such as Eudragit® E100 or EPO, tend to degrade oxycodone and that this degradation can be inhibited by providing a subcoat between the oxycodone coating and the taste-masking Eudragit® coating.

These results were confirmed by analyzing the total impurity contents of both types of tablets, after 21 days. The impurities referred to included mainly oxidation products of oxycodone, such as oxycodone N-oxide+oxymorphone, but not those coming from the synthesis of oxycodone. The tablets including a subcoat only contained 0.30% impurities at that time, whereas the comparative tablets without subcoat contained 0.49% impurities, when stored in blisters for 3 months at 40° C./75% RH.

A similar trend was observed when the tablets were stored for 28 days in an open dish instead of being kept at 80° C. dry heat in blister pockets.

Example 8

Assessment of the Stability of Oxycodone—Comparison with Tablets without Crospovidone Tablets were prepared as described in Example 2, according to the composition presented in Table 15 and compared with similar tablets which did not contain crospovidone as presented in Table 17 below.

TABLE 17

Composition of tablets without crospovidone containing taste-masked oxycodone granules with subcoat

| Materials | % |
|---|---|
| Coated oxycodone pellets (Granules D) | 7.20 |
| Coated APAP crystals (6% coating) | 26.53 |
| Mannitol 60 | 26.03 |
| Mannitol 300 | 26.04 |
| Microcrystalline cellulose PH102 | 10.00 |
| Sucralose | 1.00 |
| Prosweet | 0.38 |
| Peppermint flavor | 0.75 |
| Silicon Dioxide 244 FP | 0.50 |
| Sodium Stearyl Fumarate | 1.50 |
| Red # 40 aluminium lake | 0.07 |
| Total | 100.00 |

After 21 days at 80° C. dry heat in blister pockets, the tablets including crospovidone still contained around 95% oxycodone, whereas the comparative tablets only contained around 50% oxycodone.

This experiment makes clear that acrylic polymers bearing amino side chains, such as Eudragit® E100 or EPO, tend to degrade oxycodone (which has been confirmed by binary mixtures of Eudragit® E100 with oxycodone) and that this degradation can be inhibited under dry conditions by adding crospovidone as a disintegrant in the tablets.

These results were confirmed by analyzing the total impurity contents of both types of tablets, after 21 days. The impurities referred to included mainly oxidation products of oxycodone, such as oxycodone N-oxide+oxymorphone, but not those coming from the synthesis of oxycodone. The tablets including crospovidone only contained 0.25% impurities at that time, whereas the comparative tablets contained 7.06% impurities, as measured by HPLC.

Example 9

Assessment of the Stability—Comparison with Granules Made in an Aqueous Medium

Tablets were prepared as described in Example 2 according to the formula presented in Table 15 and compared with similar tablets in which the oxycodone coating and subcoating steps had been applied onto the neutral cores in an aqueous solvent instead of a hydroalcoholic solvent. The composition of the oxycodone taste-masked granules obtained in an aqueous solvent is given in Table 18; the tablet formula is provided in Table 19.

TABLE 18

Composition of oxycodone taste-masked granules obtained by drug loading and subcoating water-based processes

| Excipients | Weight (g) | % |
|---|---|---|
| Neutral cores | 1000.0 | 64.58 |
| Solution for drug loading | | |
| Oxycodone HCl | 39.9 | 2.58 |
| HPMC | 19.95 | 1.29 |
| Purified water | 455.77 | n/a* |
| Suspension for subcoat | | |
| HPMC | 159.0 | 10.27 |
| Syloid 244 | 15.9 | 1.03 |
| Purified water | 1574.1 | n/a* |
| Suspension for coating | | |
| Eudragit E100 | 228.3 | 14.74 |
| HPMC | 56.92 | 3.68 |
| Syloid 244 | 28.52 | 1.84 |
| Purified water | 878.5 | n/a* |
| Ethanol | 1317.7 | n/a* |
| TOTAL (Dry Mat.) | 1548.5 | 100 |

*solvent removed during process

TABLE 19

Composition of orally disintegrating tablets containing taste-masked oxycodone granules prepared by an aqueous process

| Materials | % |
|---|---|
| Coated oxycodone pellets (table 16ter) | 7.61 |
| Coated APAP crystals (6% coating) | 26.53 |
| Mannitol 60 | 18.31 |
| Mannitol 300 | 18.31 |
| Microcrystalline cellulose PH102 | 10.00 |
| Crospovidone CL | 15.00 |
| Sucralose | 1.00 |
| Prosweet | 0.38 |
| Peppermint | 0.75 |

TABLE 19-continued

Composition of orally disintegrating tablets containing taste-masked oxycodone granules prepared by an aqueous process

| Materials | % |
|---|---|
| Silicon Dioxide 244 FP | 0.50 |
| Red # 40 | 0.07 |
| Sodium Stearyl Fumarate | 0.77 |
| Lubritab | 0.77 |
| Total | 100.00 |

After 21 days at 80° C. dry heat in blister pockets, the tablets containing granules prepared with a hydroalcoholic medium contained 0.25% total impurities as defined in Examples 8 and 9, whereas the comparative tablets already included 1.14% total impurities after only 14 days.

Similarly, after 3 months storage at 40° C./75% relative humidity in blister pockets, the tablets containing granules prepared with a hydroalcoholic medium contained 0.23% of the sum of oxycodone N-oxide and oxymorphone impurities, whereas similar tablets containing granules made in an aqueous process included 1.43% of these impurities.

This experiment shows that using a hydroalcoholic drug layering process improves the stability of oxycodone in the finished tablets.

Example 10

Assessment of the Stability—Comparison with Tablets without Ascorbyl Palmitate

Two types of tablets were compared, i.e. tablets T1 similar as those described in Example 2 and corresponding tablets T2 wherein 5.04 mg (0.48% w/w) ascorbyl palmitate was added thereto.

Stability testing was conducted, according to which 0.17% impurities were detected in T1 after one month and 0.20% after two months, and the oxycodone value had dropped to 96% in these tablets. On the contrary, 0% impurities were detected in T2 even after three months, and the oxycodone content was stable during this period.

The invention claimed is:

1. A granule consisting essentially of a neutral core coated by: (a) oxycodone or a pharmaceutically acceptable salt of oxycodone, and (b) at least a binding agent, said oxycodone coating being further coated by a subcoat consisting of a compound soluble in gastric fluids and optionally an antistatic agent, wherein said subcoat is further coated by a taste-masking coating consisting of a polymer or copolymer with dialkylaminoalkyl(meth)acrylate units, which is insoluble at a pH above 5.5 but is soluble in gastric juice, and optionally an antistatic agent or a pore-forming agent, wherein the subcoat is adapted to avoid direct contact between the oxycodone or the pharmaceutically acceptable salt of oxycodone and the taste-masking coating such that degradation of oxycodone is inhibited.

2. The granule according to claim 1, wherein the oxycodone comprises oxycodone hydrochloride.

3. The granule according to claim 1, wherein the compound soluble in gastric fluid and the binder are independently selected from the group consisting of: cellulose-based polymers; polyvinyl alcohols; alginic acid; sodium alginate; starch; pregelatinized starch; sucroses; sucrose derivatives; guar gum; polyethylene glycols; and mixtures and copolymers thereof.

4. The granule according to claim 3, wherein the compound soluble in gastric fluid is a cellulose-based polymer selected from the group consisting of hydroxypropylmethylcellulose polymer, hydroxypropylcellulose polymer and hydroxyethylcellulose acrylic polymer.

5. The granule according to claim 1, wherein the polymer or copolymer with dialkylaminoalkyl(meth)acrylate units is a copolymer of dimethylaminoethyl methacrylate, methylmethacrylate and n-butyl methacrylate.

6. The granule according to claim 1, wherein the pore-forming agent is hydroxypropylmethylcellulose.

7. A process for the manufacture of granules according to claim 1, wherein a suspension of oxycodone in a hydroalcoholic medium is sprayed onto neutral cores.

8. An orally disintegrating tablet comprising: (a) granules consisting essentially of a neutral core coated by: (a) oxycodone or a pharmaceutically acceptable salt of oxycodone, and (b) at least a binder, said oxycodone coating being further coated by a subcoat consisting of a compound soluble in gastric fluid and optionally an antistatic agent; wherein said subcoat is further coated by a taste-masking coating consisting of a polymer or copolymer with dialkylaminoalkyl(meth)acrylate units, which is insoluble at a pH above 5.5 but is soluble in gastric juice, and optionally an antistatic or a pore-forming agent, wherein the subcoat is adapted to avoid direct contact between the oxycodone or the pharmaceutically acceptable salt of oxycodone and the taste-masking coating such that degradation of oxycodone is inhibited and (b) at least one disintegrant and at least one diluent, wherein said disintegrant comprises crospovidone.

9. The orally disintegrating tablet according to claim 8, further comprising an anti-oxidant agent.

10. The orally disintegrating tablet according to claim 9, wherein the anti-oxidant agent is ascorbyl palmitate.

11. An orally disintegrating tablet comprising: (a) granules consisting essentially of a neutral core coated by: (i) oxycodone or a pharmaceutically acceptable salt of oxycodone, and (ii) at least one binding agent, said oxycodone coating being further coated by a subcoat consisting of a compound soluble in gastric fluid and optionally an antistatic agent; wherein said subcoat is further coated by a taste-masking coating consisting of a polymer or copolymer with dialkylaminoalkyl(meth)acrylate units, which is insoluble at a pH above 5.5 but is soluble in gastric juice, and optionally an antistatic or a pore-forming agent, wherein the subcoat is adapted to avoid direct contact between the oxycodone or the pharmaceutically acceptable salt of oxycodone and the taste-masking coating such that degradation of oxycodone is inhibited (b) acetaminophen which is not included within said granules, and (c) at least one disintegrant and at least one soluble diluent agent, wherein said disintegrant comprises crospovidone.

12. The orally disintegrating tablet according to claim 11, wherein the compound soluble in gastric fluids is selected from the group consisting of: cellulose-based polymers; polyvinyl alcohols; alginic acid; sodium alginate; starch; pregelatinized starch; sucroses; sucrose derivatives; guar gum; polyethylene glycols, and mixtures and copolymers thereof.

13. The orally disintegrating tablet according to claim 12, wherein the compound soluble in gastric fluid is hydroxypropylmethylcellulose polymer, hydroxypropylcellulose polymer or hydroxyethylcellulose acrylic polymer.

14. The orally disintegrating tablet according to claim 11, further comprising an anti-oxidant agent.

15. The orally disintegrating tablet according to claim 14, wherein the anti-oxidant agent is ascorbyl palmitate.

16. The orally disintegrating tablet according to claim 11, wherein the pore-forming agent is hydroxypropylmethylcellulose.

17. The orally disintegrating tablet according to claim 11, comprising from 2.5 to 10 mg oxycodone and from 80 to 750 mg acetaminophen.

18. A method for reducing pain in a patient, comprising oral administration to said patient of granules according to claim 1.

19. The method for reducing pain in a patient, comprising oral administration to said patient of a tablet according to claim 8.

20. A process for manufacturing an orally disintegrating tablet according to claim 8, comprising the steps of:
  (a) spraying onto neutral cores a suspension in a solvent comprising: (i) oxycodone or a pharmaceutically acceptable salt of oxycodone, and (ii) at least one binding agent, so as to obtain pellets,
  (b) applying the subcoat onto said pellets to obtain coated pellets,
  (c) optionally drying said coated pellets,
  (d) applying onto said coated pellets the taste-masking coating to obtain granules,
  (e) optionally applying an antistatic coating onto said granules,
  (f) mixing acetaminophen with said granules, at least one disintegrant comprising crospovidone and at least one diluent agent, so as to obtain a mixture, and
  (g) tableting said mixture,
wherein the solvent used in at least one of steps (a) and (b) is a hydroalcoholic solvent.

21. The orally disintegrating tablet according to claim 11 comprising acetaminophen and oxycodone as the only active ingredients, said tablet having an oxycodone content, after dry storage at 80° C. for 14 days of at least 90% of the initial oxycodone content before storage.

22. A granule consisting essentially of a neutral core coated by: (a) oxycodone or a pharmaceutically acceptable salt of oxycodone, and (b) at least a binding agent, said oxycodone coating being further coated by a subcoat consisting of a compound soluble in gastric fluids and optionally an antistatic agent, wherein said subcoat is further coated by a taste-masking coating consisting of a polymer or copolymer with dialkylaminoalkyl(meth)acrylate units which is insoluble at a pH above 5.5 but is soluble in gastric juice, and optionally an antistatic agent or a pore-forming agent, wherein the subcoat is adapted to avoid direct contact between the oxycodone or the pharmaceutically acceptable salt of oxycodone and the taste-masking coating such that at least 90% of oxycodone or pharmaceutically acceptable salt of oxycodone remains after storage for 14 days at 80° C. dry heat.

23. An orally disintegrating tablet comprising: (a) granules consisting essentially of a neutral core coated by: (i) oxycodone or a pharmaceutically acceptable salt of oxycodone, and (ii) at least a binder, said oxycodone coating being further coated by a subcoat consisting of a compound soluble in gastric fluid and optionally an antistatic agent; wherein said subcoat is further coated by a taste-masking coating consisting of a polymer or copolymer with dialkylaminoalkyl(meth)acrylate units which is insoluble at a pH above 5.5 but is soluble in gastric juice and optionally an antistatic or a pore-forming agent, wherein the subcoat is adapted to avoid direct contact between the oxycodone or the pharmaceutically acceptable salt of oxycodone and the taste-masking coating such that at least 90% of oxycodone or pharmaceutically acceptable salt of oxycodone remains after storage for 14 days at 80° C. dry heat and (b) at least one disintegrant and at least one diluent, wherein said disintegrant comprises crospovidone.

24. An orally disintegrating tablet comprising: (a) granules consisting essentially of a neutral core coated by: (i) oxycodone or a pharmaceutically acceptable salt of oxycodone, and (ii) at least one binding agent, said oxycodone coating being further coated by a subcoat consisting of a compound soluble in gastric fluid and optionally an antistatic agent; wherein said subcoat is further coated by a taste-masking coating consisting of a polymer or copolymer with dialkylaminoalkyl(meth)acrylate units, which is insoluble at a pH above 5.5 but is soluble in gastric juice, and optionally an antistatic or a pore-forming agent, wherein the subcoat is adapted to avoid direct contact between the oxycodone or the pharmaceutically acceptable salt of oxycodone and the taste-masking coating such that at least 90% of oxycodone or pharmaceutically acceptable salt of oxycodone remains after storage for 14 days at 80° C. dry heat; (b) acetaminophen which is not included within said granules; and (c) at least one disintegrant and at least one diluent agent, wherein said disintegrant comprises crospovidone.

\* \* \* \* \*